United States Patent
Capron et al.

(10) Patent No.: US 9,593,313 B2
(45) Date of Patent: Mar. 14, 2017

(54) 28 KDA GST PROTEINS FROM SCHISTOSOMA FOR THE USE THEREOF IN THE TREATMENT OF INFLAMMATORY AUTOIMMUNE DISEASES GENERATING A TH1 AND/OR TH17 RESPONSE

(71) Applicants: UNIVERSITE DU DROIT ET DE LA SANTE DE LILLE 2, Lille (FR); INSERM (INSTITUT NATIONAL DE LA SANTE ET DE LA RECHERCHE MEDICALE, Paris (FR); CENTRE NATIONAL DE LA RECHERCHE SCIENTIFIQUE, Paris (FR); CENTRE HOSPITALIER REGIONAL UNIVERSITAIRE DE LILLE, Lille (FR)

(72) Inventors: Monique Capron, Phalempin (FR); Mohamed El Nady, Wattignies (FR); Jean-Frederic Colombel, Lille (FR); Gilles Riveau, Phalempin (FR)

(73) Assignees: UNIVERSITE DU DROIT ET DE LA SANTE DE LILLE 2, Lille (FR); INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 0 days.

(21) Appl. No.: 14/377,006

(22) PCT Filed: Feb. 6, 2013

(86) PCT No.: PCT/FR2013/050252
§ 371 (c)(1),
(2) Date: Aug. 6, 2014

(87) PCT Pub. No.: WO2013/117860
PCT Pub. Date: Aug. 15, 2013

(65) Prior Publication Data
US 2015/0118259 A1  Apr. 30, 2015

(30) Foreign Application Priority Data
Feb. 6, 2012  (FR) ..................... 12 51100

(51) Int. Cl.
*A61K 39/00* (2006.01)
*C12N 9/10* (2006.01)
*A61K 38/45* (2006.01)
*C07K 14/00* (2006.01)
*A61K 39/002* (2006.01)

(52) U.S. Cl.
CPC ............ *C12N 9/1088* (2013.01); *A61K 38/45* (2013.01); *A61K 39/002* (2013.01); *C07K 14/00* (2013.01); *A61K 2039/55505* (2013.01); *A61K 2039/57* (2013.01)

(58) Field of Classification Search
None
See application file for complete search history.

(56) References Cited

FOREIGN PATENT DOCUMENTS

FR  2 688 008 A1  9/1993

OTHER PUBLICATIONS

Ritter et al. Proceedings of the National Academy of Sciences, vol. 107, No. 47, 2010.*
Li Guang-Fu et al.: "Identification of immunodominant Th1-type T cell epitopes from Schistosoma japonicum 28 kDa glutathione-S-transferase, a vaccine candidate", Acta Biochimica et Biophysica Sinica, vol. 37, No. 11, Nov. 2005 (Nov. 2005), pp. 751-758, XP002674842, ISSN: 1672-9145 abstract.
Allameh A. et al.: "The influence of uric acid treatments on liver glutathione system prevent oxidative damages in experimental autoimmune encephalomyelitis mice", Neuroscience Letters Jul. 4, 2008 IE LNKDDOI: 10.1016/J.NEULET.2008.04.053, vol. 439, No. 1,Jul. 4, 2008 (Jul. 4, 2008), pp. 111-115, XP002674843, ISSN: 0304-3940 abstract.
Herve Maxime et al.: "Pivotal roles of the parasite PGD2 synthase and of the host D prostanoid receptor 1 in schistosome immune evasion.", European Journal of Immunology, vol. 33, No. 10, Oct. 2003 (Oct. 2003), pp. 2764-2772, XP002674844, ISSN: 0014-2980 abstract.
Osada Yoshio et al.: "Parasitic Helminths:New Weapons against Immunological Disorders", Journal of Biomedicine & Biotechnology, 2010, XP002696665, the whole document.
El-Malky M et al.: "Helminth infections: therapeutic potential in autoimmune disorders", Parasite Immunology (Oxford), vol. 33, No. 11, Nov. 2011 (Nov. 2011), pp. 589-593, XP002696666, the whole document.
International Search Report, dated May 21, 2013, from corresponding PCT application.
FR Search Report, dated Apr. 26, 2012, from corresponding FR application.

* cited by examiner

Primary Examiner — J. Hines
Assistant Examiner — Khatol Shahnan Shah
(74) Attorney, Agent, or Firm — Young & Thompson

(57) ABSTRACT

The present invention relates to a product selected from a protein, a fragment of the protein, a derived sequence and a homologous sequence of the protein, the protein including or being constituted by the 28 kDa glutathione S-transferase protein from a schistosome selected from *Schistosoma haematobium*, *Schistosoma mansoni*, *Schistosoma bovis* represented respectively by the sequences SEQ ID NO: 1, SEQ ID NO: 2 and SEQ ID NO: 3 for the use thereof in the treatment of an inflammatory autoimmune disease generating a response of type Th1 and/or Th17.

10 Claims, 14 Drawing Sheets

Figure 1:
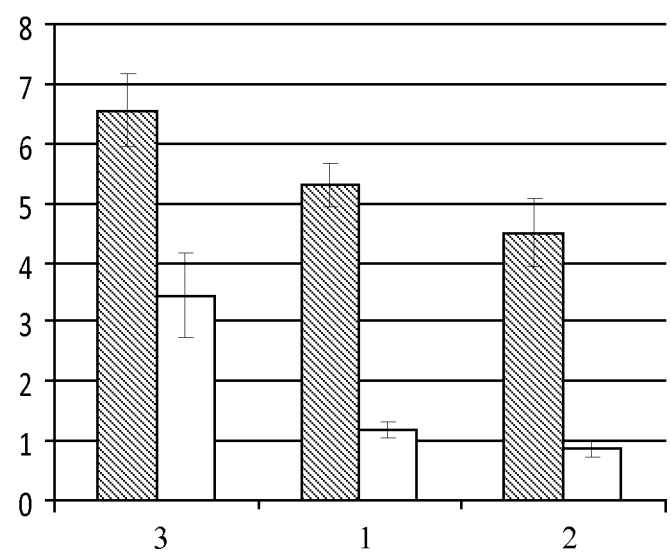

28 KDA GST PROTEINS FROM SCHISTOSOMA FOR THE USE THEREOF IN THE TREATMENT OF INFLAMMATORY AUTOIMMUNE DISEASES GENERATING A TH1 AND/OR TH17 RESPONSE

The present invention relates to particular proteins which are glutathione-S-transferases originating from various schistosome parasites, for the use thereof in the treatment of autoimmune inflammatory diseases such as Crohn's disease or multiple sclerosis. The present invention also relates to the fragments of said proteins, the sequences derived from these proteins and homologues of these proteins in so far as these sequences and these fragments may generate an anti-inflammatory response.

The present invention also relates to a pharmaceutical composition comprising the aforementioned objects and at least one pharmacologically acceptable excipient.

In the developed countries, chronic inflammatory diseases connected with an immune system disorder (autoimmune inflammatory diseases) affect about 8% of the population. Among the commonest autoimmune inflammatory diseases, there may be mentioned chronic inflammatory bowel diseases (CIBDs) and multiple sclerosis.

Chronic inflammatory bowel diseases (Crohn's disease and ulcerative colitis) are becoming more and more frequent in the so-called "developed" countries. Recently, unfortunately, we have witnessed an increase in paediatric cases of these pathologies in these countries. Moreover, these diseases are beginning to make an appearance in the so-called "developing" countries, probably owing to changes in eating habits and sanitary conditions. The conventional treatments of chronic autoimmune inflammatory diseases are based on immunosuppressants and/or corticosteroids. These treatments are not without serious side-effects.

Thus, with regard to Crohn's disease, azathioprine, methotrexate or ciclosporin, which are immunosuppressants, display variable efficacy and may be associated with serious side-effects such as lymphocytosis syndromes or hepatic fibroses.

The acute forms of Crohn's disease are treated with corticosteroids, which have high toxicity and promote the development of osteoporosis, diabetes and opportunistic infections.

Biological therapies utilize the inhibition of TNF via anti-TNF monoclonal antibodies. These therapies make it possible to reduce hospitalizations and surgical interventions but give rise to risks of infection, lymphoma or heart failure. Moreover, some patients are unresponsive to this type of therapy, which moreover remains very expensive. Furthermore, each recurrence of the disease risks generating disabling consequences for the patient, for example fitting a bag for the collection of faeces. The patient's quality of life is greatly reduced.

In the paediatric forms of these diseases, and especially in the case of Crohn's disease, the incidence of which has increased considerably in the last ten years, the therapeutic armamentarium is very limited. Immunosuppressants cannot be used.

There is therefore a real and urgent need to develop a novel preventive and/or therapeutic treatment for chronic inflammatory diseases connected with an immune system disorder generating an inflammatory response of type Th1 and/or Th17, such as Crohn's disease or multiple sclerosis, for example.

A first purpose of the present invention is to propose a novel active ingredient for use in the preventive and/or therapeutic treatment of chronic inflammatory diseases generating an inflammatory response of type Th1 and/or Th17.

Another purpose of the present invention is to propose an active ingredient for use in the preventive and/or therapeutic treatment of the aforementioned diseases that displays low toxicity and little or no side-effects.

Another purpose of the present invention is to propose an active ingredient for use in the treatment of the aforementioned diseases that can be administered to children.

At least one of these purposes is achieved by means of a product selected from a protein, a fragment of said protein, a derived sequence and a homologous sequence of said protein. According to the invention, characteristically, said protein comprises or is constituted by the 28 kDa glutathione S-transferase protein from a schistosome selected from *Schistosoma haematobium, Schistosoma mansoni, Schistosoma bovis* represented by the sequences SEQ ID NO: 1, SEQ ID NO: 2, and SEQ ID NO: 3, respectively;

said fragment is a fragment of one of said proteins provided that it induces a type-Th2 immune response, said fragment preferably comprising at least the region comprised from the amino acid in position 15 to the amino acid in position 60, in particular the region comprised from the amino acid in position 20 to the amino acid in position 50, preferably the region comprised from the amino acid in position 24 to the amino acid in position 43 and the region comprised from the amino acid in position 170 to the amino acid in position 220, in particular the region comprised from the amino acid in position 180 to the amino acid in position 215, preferably the region comprised from the amino acid in position 190 to the amino acid in position 211 of the sequence SEQ ID NO: 1, SEQ ID NO: 2 or SEQ ID NO: 3;

said derived sequence is derived from one of said sequences SEQ ID NO: 1, SEQ ID NO: 2 and SEQ ID NO: 3 or of said aforementioned fragments and in particular is obtained by suppression, substitution or addition of one or more amino acids, provided that this derived sequence induces a type-Th2 response;

said homologous sequence is a homologous sequence of one of said sequences SEQ ID NO: 1, SEQ ID NO: 2 and SEQ ID NO: 3 or of one of said fragments, and in particular has an identity of at least 80% and in particular of at least 85% with one of said sequences SEQ ID NO: 1, SEQ ID NO: 2 and SEQ ID NO: 3, provided that said homologous sequence induces a type-Th2 response; for use in the preventive and/or therapeutic treatment of a chronic inflammatory disease connected with an immune system disorder generating an immune response of type Th1/Th17.

According to a particular embodiment, the invention relates to a product selected from a protein, a fragment of said protein, a derived sequence and a homologous sequence of said protein, and characteristically:

said protein comprises or is constituted by the 28 kDa glutathione S-transferase protein from a schistosome selected from *Schistosoma haematobium, Schistosoma mansoni, Schistosoma bovis* represented by the sequences SEQ ID NO: 1, SEQ ID NO: 2, and SEQ ID NO: 3, respectively;

said fragment is a fragment of one of said proteins provided that it induces a type-Th2 immune response and/or decreases the Th1-type response, said fragment comprising at least one region from among the following regions: the region comprised from the amino acid in position 15 to the amino acid in position 60, the region comprised from the amino acid in position 20 to the amino acid in position 50, the region comprised from the amino acid in position 24 to the amino acid in position 43, the region comprised from the amino acid in position 170 to the amino acid in position 220, in particular the region comprised from the amino acid in position 180 to the amino acid in position 215, preferably the region comprised from the amino acid in position 190 to the amino acid in position 211 of the sequence SEQ ID NO: 1, SEQ ID NO: 2 or SEQ ID NO: 3;

said derived sequence is derived from one of said sequences SEQ ID NO: 1, SEQ ID NO: 2 and SEQ ID NO: 3 or from one of said aforementioned fragments and in particular is obtained by suppression, substitution or addition of one or more amino acids, in the sequence SEQ ID NO: 1, SEQ ID NO: 2 or SEQ ID NO: 3, said derived sequence comprising at least one region from among the following regions: the region comprised from the amino acid in position 15 to the amino acid in position 60, the region comprised from the amino acid in position 20 to the amino acid in position 50, the region comprised from the amino acid in position 24 to the amino acid in position 43, the region comprised from the amino acid in position 170 to the amino acid in position 220, the region comprised from the amino acid in position 180 to the amino acid in position 215 and the region comprised from the amino acid in position 190 to the amino acid in position 211 of the sequence SEQ ID NO: 1, SEQ ID NO: 2 or SEQ ID NO: 3; thereby leading to the induction of a Th2 response and/or the decrease of the Th1 response; and said homologous sequence is a homologous sequence of one of said sequences SEQ ID NO: 1, SEQ ID NO: 2 and SEQ ID NO: 3 or of one of said fragments, and has an identity of at least 80% and in particular of at least 85% with at least one of the following regions of said sequences: the region comprised from the amino acid in position 15 to the amino acid in position 60, the region comprised from the amino acid in position 20 to the amino acid in position 50, the region comprised from the amino acid in position 24 to the amino acid in position 43, the region comprised from the amino acid in position 170 to the amino acid in position 220, the region comprised from the amino acid in position 180 to the amino acid in position 215, and the region comprised from the amino acid in position 190 to the amino acid in position 211 of the sequence SEQ ID NO: 1, SEQ ID NO: 2 or SEQ ID NO: 3; or with the whole of one of the sequences SEQ ID NO: 1, SEQ ID NO: 2 or SEQ ID NO: 3; thereby leading to the induction of a Th2 response and/or the decrease of the Th1 response, for the use thereof in the preventive and/or therapeutic treatment of a chronic inflammatory disease connected with an immune system disorder generating an immune response of type Th1/Th17.

According to the invention the fragment is a fragment of one of said proteins and preferably comprises at least the region comprised from the amino acid in position 15 to the amino acid in position 60, in particular the region comprised from the amino acid in position 20 to the amino acid in position 50, preferably the region comprised from the amino acid in position 24 to the amino acid in position 43 and the region comprised from the amino acid in position 170 to the amino acid in position 220, in particular the region comprised from the amino acid in position 180 to the amino acid in position 215, preferably the region comprised from the amino acid in position 190 to the amino acid in position 211 of the sequence SEQ ID NO: 1, SEQ ID NO: 2 or SEQ ID NO: 3, thereby leading to the induction of a Th2 response and/or the decrease of the Th1 response.

When the product of the invention is a sequence derived from one of said sequences SEQ ID NO: 1, SEQ ID NO: 2 and SEQ ID NO: 3, said derived sequence may advantageously comprise at least the region comprised from the amino acid in position 15 to the amino acid in position 60, in particular the region comprised from the amino acid in position 20 to the amino acid in position 50, preferably the region comprised from the amino acid in position 24 to the amino acid in position 43 and the region comprised from the amino acid in position 170 to the amino acid in position 220, in particular the region comprised from the amino acid in position 180 to the amino acid in position 215, preferably the region comprised from the amino acid in position 190 to the amino acid in position 211 of the sequence SEQ ID NO: 1, SEQ ID NO: 2 or SEQ ID NO: 3, thereby inducing a Th2 response and/or the decrease of the Th1 response.

When the product of the invention is a homologous sequence as mentioned above, it advantageously comprises at least the region comprised from the amino acid in position 15 to the amino acid in position 60, in particular the region comprised from the amino acid in position 20 to the amino acid in position 50, preferably the region comprised from the amino acid in position 24 to the amino acid in position 43 and the region comprised from the amino acid in position 170 to the amino acid in position 220, in particular the region comprised from the amino acid in position 180 to the amino acid in position 215, preferably the region comprised from the amino acid in position 190 to the amino acid in position 211 of the sequence SEQ ID NO: 1, SEQ ID NO: 2 or SEQ ID NO: 3, thereby inducing a Th2 response and/or the decrease of the Th1 response.

The homologous sequence may therefore comprise at least one of the aforementioned regions or all the aforementioned regions. These regions may be identical to the corresponding regions of sequences SEQ ID NO: 1, SEQ ID NO: 2 and SEQ ID NO: 3 or may each have a homology of at least 80% and preferably of at least 85% with the corresponding region of one of the aforementioned sequences. The percentage homology may be different for each region.

According to the present invention, a Th1-type response is defined as being characterized by the presence of lymphocytes producing cytokines such as IFN gamma but not producing IL-4 or IL-5. This response also leads to the production of TNF.

A type-Th2 response is characterized by the presence of lymphocytes producing cytokines such as IL-4, IL-5 or IL-13 but without producing IFN gamma.

The response of type Th17 is an inflammatory response where the lymphocytes produce IL-17 or IL-25, in addition to the TNF produced by many cellular types.

Therefore the type of response is measured by evaluating the cytokines produced either by the cells themselves (by flow cytometry) when we have access to the cells, or by PCR in the tissues. When "type" of response is mentioned; the type of response corresponds to the predominant response of the cells or of the organism. In practice, there are always mixed responses. One means for measuring the Th1 response versus Th2 is to measure the IFNgamma/IL-4 ratio.

The autoimmune pathologies often generate mixed responses and especially pro-inflammatory responses, hence the use of biotherapies based on anti-TNF.

According to one embodiment, said protein is represented by the sequence SEQ ID NO: 1 (28 GST glutathione transferase from *Schistosoma haematobium*), said fragment is a fragment of said protein in particular comprising the region comprised from the amino acid in position 15 to the amino acid in position 60, in particular the region comprised from the amino acid in position 20 to the amino acid in position 50, preferably the region comprised from the amino acid in position 24 to the amino acid in position 43 and the region comprised from the amino acid in position 170 to the amino acid in position 220, in particular the region comprised from the amino acid in position 180 to the amino acid in position 215, preferably the region comprised from the amino acid in position 190 to the amino acid in position 211, said derived sequence is obtained from SEQ ID NO: 1 and said homologous sequence has an identity as mentioned above with the sequence SEQ ID NO: 1.

According to another particular embodiment, said product is the expression product of a nucleotide sequence coding for:
the 28 kDa glutathione-S-transferase protein represented by SEQ ID NO: 1; or
a fragment of said protein represented by SEQ ID NO: 1, said fragment comprising or being constituted by at least the region comprised from the amino acid in position 15 to the amino acid in position 60, in particular the region comprised from the amino acid in position 20 to the amino acid in position 50, preferably the region comprised from the amino acid in position 24 to the amino acid in position 43 and the region comprised from the amino acid in position 170 to the amino acid in position 220, in particular the region comprised from the amino acid in position 180 to the amino acid in position 215, preferably the region comprised from the amino acid in position 190 to the amino acid in position 211 of the sequence SEQ ID NO: 1; or
a derived sequence such as mentioned above; or
a homologous sequence such as mentioned above;
said coding nucleotide sequence in particular corresponding to sequence SEQ ID NO: 4.

According to a particular embodiment, the protein is the expression product of said coding sequence SEQ ID NO: 4 in *Saccharomyces cerevisiae* or in *Escherichia coli*.

According to the invention, the disease defined above is selected from the following autoimmune inflammatory diseases: Berger's disease, Basedow's disease, Hashimoto's thyroiditis, primary myxoedema, coeliac disease, ulcerative colitis, Crohn's disease, rheumatoid arthritis, primary biliary cirrhosis, primary sclerosing cholangitis, autoimmune haemolytic anaemias, Biermer's anaemia (pernicious anaemia), lupus erythematosus, CREST syndrome, type 1 diabetes, scleroderma, pemphigus vulgaris, bullous pemphigoid, acquired epidermolysis bullosa, dermatitis herpetiformis, myasthenia, Lambert-Eaton myasthenic syndrome, polymyositis, Goujerot-Sjögren syndrome, multiple sclerosis, Graves' disease and psoriasis.

According to the invention, treatment of the aforementioned pathology may apply to any patient, human or animal. It applies in particular to a human being, adult or child. According to the invention, the treatment may relate more particularly to a child and more particularly the preventive treatment of children.

"Child" is defined as an individual aged from 0 to 18 years, more particularly aged from 9 to 18 years.

The present invention also relates to a pharmaceutical composition, said composition comprising, as active ingredient, a product according to the invention and a pharmacologically acceptable excipient, in particular for the preventive and/or therapeutic treatment of a chronic inflammatory disease connected with an autoimmune disorder generating an immune response of type Th1 and/or Th17.

By "pharmacologically acceptable" is meant, within the meaning of the present invention, any excipient that may be injected, ingested or at least applied on the skin without producing a secondary reaction that is greater, statistically, than the benefit afforded by the treatment.

According to the invention, the composition is used advantageously in the preventive and/or therapeutic treatment of a disease selected from the following autoimmune inflammatory diseases: Berger's disease, Basedow's disease, Hashimoto's thyroiditis, primary myxoedema, coeliac disease, ulcerative colitis, Crohn's disease, rheumatoid arthritis, primary biliary cirrhosis, primary sclerosing cholangitis, autoimmune haemolytic anaemias, Biermer's anaemia (pernicious anaemia), lupus erythematosus, CREST syndrome, type 1 diabetes, scleroderma, pemphigus vulgaris, bullous pemphigoid, acquired epidermolysis bullosa, dermatitis herpetiformis, myasthenia, Lambert-Eaton myasthenic syndrome, polymyositis, Goujerot-Sjögren syndrome, multiple sclerosis, rheumatoid arthritis, Graves' disease and psoriasis, in particular the paediatric forms of these pathologies, when they exist, and in particular treatment for preventive purposes and more particularly the preventive treatment of the paediatric forms.

The immunogenic action of the product and/or of the composition according to the invention may be the reduction or suppression of the inflammatory reaction (in particular of type Th1) and/or the induction of a type-Th2 immune response via, for example, the secretion of certain interleukins.

The present invention also relates to said pharmaceutical composition as a vaccine and usable for treating an autoimmune disease generating a response of type Th1 and/or Th17 and in particular for treating the aforementioned pathologies. This vaccine may be intended in particular for children.

According to the invention, the composition may comprise an adjuvant, in particular an adjuvant selected from the aluminium salts and more particularly aluminium hydroxide. Aluminium hydroxide is an adjuvant of the immune response used in vaccinology and is compatible with human use. Forming an ionic network, the antigenic proteins are adsorbed there after incubation for a few minutes. This complex creates a temporary store allowing cellular recruitment and promoting the antigenic type-Th2 response.

The term "aluminium salts" denotes all the natural or non-natural aluminium salts. It is, for example, aluminium sulphate (hydrated or not), aluminium phosphate, alum $(KAl(SO_4)_2.12H_2O)$, aluminium hydroxide or any other salt of formula $(BAl(SO_4)_2.12H_2O)$.

According to the invention, the concentration of adjuvant is comprised from 0.5 mg/ml to 2 mg/ml, in particular from 0.3 mg/ml to 1 mg/ml and in particular from 220 μg/ml to 280 μg/ml and preferably approximately equal to 250 μg/ml.

As illustrated below, good results are obtained with aluminium hydroxide at a concentration comprised within the range of concentrations mentioned above and in particular at 250 μg/ml.

The present invention also relates to a product selected from a protein, a fragment of said protein, a derived sequence and a homologous sequence of said protein, characterized in that:

said protein comprises or is constituted by the 28 kDa glutathione S-transferase protein from *Schistosoma japonicum* or the 26 kDa glutathione S-transferase protein from *Schistosoma japonicum* represented by the sequences SEQ ID NO: 5, and SEQ ID NO: 6, respectively, in that said fragment is a fragment of one of said proteins provided that it mainly induces a type-Th2 immune response, in that said derived sequence is derived from one of said sequences SEQ ID NO: 5, and SEQ ID NO: 6 or from said aforementioned fragments and in particular is obtained by suppression, substitution or addition of one or more amino acids, provided that this derived sequence mainly induces a type-Th2 response, and in that said homologous sequence is a homologous sequence of one of said sequences SEQ ID NO: 5, and SEQ ID NO: 6 or of one of said fragments, and in particular has an identity of at least 80% and in particular of at least 85% with one of said sequences SEQ ID NO: 5, and SEQ ID NO: 6, provided that said homologous sequence mainly induces a type-Th2 response; for the use thereof in the preventive and/or therapeutic treatment of a chronic inflammatory disease connected with an immune system disorder generating an immune response of type Th1 and/or Th17, in particular in a child.

The chronic inflammatory disease connected with an immune system disorder generating an immune response of type Th1 and/or Th17 may be selected from Crohn's disease, ulcerative colitis, multiple sclerosis, rheumatoid arthritis, type 1 (autoimmune) diabetes, Graves' disease and psoriasis.

The present invention also relates to a pharmaceutical composition comprising as active ingredient at least one of the products as mentioned above with reference to Sj28GST and Sj26GST and a pharmacologically acceptable excipient.

This composition may also comprise an adjuvant such as mentioned above and in particular aluminium hydroxide. The quantity of adjuvant may be as mentioned above.

The 28 kDa glutathione S-transferase native protein is a protein expressed by the schistosome parasites, flatworms responsible for schistosomiasis. There are several species of schistosomes. *Schistosoma mansoni* is responsible in humans for intestinal schistosomiasis, in Africa and Brazil. *Schistosoma haematobium* is responsible in humans for urinary schistosomiasis in Africa and the Arabian Peninsula. Each schistosome species expresses its own characteristic 28 kDa glutathione S-transferase. Thus, the species *Schistosoma mansoni* expresses Sm28GST, the species *Schistosoma haematobium* expresses Sh28GST, *Schistosoma bovis* (a schistosome infecting livestock) expresses Sb28GST and the species *Schistosoma japonicum* (affecting South East Asia—the Philippines and South China—) expresses Sj28GST and Sj26GST. The genes encoding these proteins are known and/or a person skilled in the art is capable of identifying them. A person skilled in the art is therefore able to produce the aforementioned proteins and the products of the invention by recombinant techniques.

The Sh28GST, Sm28GST, Sb28GST, Sj28GST and Sj26GST proteins have sequences that are identified and listed in the databases, in particular on the website UniProt.

The Sb28GST and Sh28GST proteins are 97% identical whereas the Sh28GST and Sm28GST proteins are 91% identical.

The sequences SEQ ID NO: 1, SEQ ID NO: 2, SEQ ID NO: 3, SEQ ID NO: 5 and SEQ ID NO: 6 hereunder represent the sequences of the Sh28GST, Sm28GST, Sb28GST, Sj28GST and Sj26GST proteins, respectively.

It is known that parasites induce an immune response in the infested host. Thus, it is known that the schistosome has an effect on the immune system of the host that it infests so that the latter does not reject it. The immune reaction of the host begins with a reaction of type Th1, of short duration, then continues with a reaction of type Th2 and finally with a regulatory T reaction. When the regulatory T response is produced, the infected host and the parasite coexist.

It is known that the chronic inflammatory diseases connected with an immune system disorder generate an abnormal immune response to auto-antigens in the patient, and this induces inflammation. In the case of Crohn's disease and ulcerative colitis, inflammation of the intestinal mucosa is observed, characterized by ulcerations and infiltration of the inflammatory cells recruited by cytokines and chemoattractants of type Th1, among others.

In the case of multiple sclerosis, local inflammation of the myelin sheath of the axons of the brain and spinal cord is observed, which generates demyelination of the nerve fibres.

The inventors have shown that, surprisingly, the Sh28GST protein makes it possible, by generating an anti-inflammatory type-Th2 response, to reduce the Th1-type response. This decrease in the Th1-type response makes it possible to reduce the symptoms associated with the aforementioned disease, in particular the inflammation. Acting in particular on the interleukins that are present throughout the body, the protein can therefore be used for the preventive or therapeutic treatment of a disease such as mentioned above affecting any organ or even the whole body. The same effects may be envisaged for all the products of the invention.

Moreover, it is known that there is a connection between inflammation and cancer, the first promoting development of the second. The protein according to the invention may thus, by directly or indirectly reducing chronic inflammation, reduce or even eliminate cancers induced by the chronic inflammation associated with inflammatory autoimmune disease. Thus, ulcerative colitis and Crohn's disease are factors of increased risk for colorectal cancer.

The results given below confirm the effect of the Sh28GST protein in the treatment (in particular preventive) of Crohn's disease, which is an inflammatory autoimmune disease generating a Th1-type response.

The protein according to the invention, regardless of the schistosome from which it is derived and regardless of its molecular weight, may be natural isolated (native) or recombinant.

Throughout the present patent application, the term "recombinant 28 kDa glutathione S-transferase" (rSh28GST) denotes any protein obtained recombinantly by inserting the complete sequence coding for Sh28GST (SEQ NO: 4) or a fraction of this sequence into a host organism. This synthesis may be carried out in various host cells, bacteria, yeasts or higher cells, as a function of the vector into which the coding sequence is inserted and the signals controlling expression. The recombinant protein according to the present invention may have a primary structure identical to that of the Sh28GST native protein, present in *Schistosoma haematobium*, but it may also be a derivative of the latter or an Sh28GST incomplete protein (protein fragment), but having immunogenic activity. This protein or this protein fragment may also be fused with another protein (or protein fragment), following genetic manipulation of the corresponding DNA segments, in order to promote better expression of the protein in the host cell or optionally to cause its excretion out of the cell.

In the examples, the term rSh28GST denotes the protein produced in *Saccharomyces cerevisiae* by inserting the coding nucleotide sequence SEQ NO: 4.

The rSh28GST protein is well known. Thus, the aforementioned article "Crystal structure of the 28 kDa glutathione S-transferase from *Schistosoma haematobium*" cites a method of producing the recombinant Sh28GST according to the invention in *Escherichia coli*. Moreover, the article "Vaccine potential of a recombinant glutathione S-transferase cloned from *Schistosoma haematobium* in primates experimentally infected with an homologous challenge", published in the journal Vaccine in 1999, cites a Sh28GST recombinant protein produced in a specific strain of *Saccharomyces cerevisiae*.

However, the recombinant protein of the invention is not limited to these two examples mentioned above, as the technologies for cloning and expressing a foreign gene or a foreign gene fragment in various host cells are known to a person skilled in the art.

Production of the recombinant protein in these bacteria is already known and perfectly mastered. In fact, the rSh28GST recombinant protein is the object of clinical trials for vaccination against schistosomiasis (Bilhvax project). This recombinant protein is therefore produced on an industrial scale; its production and its purification, in particular for therapeutic purposes, are therefore perfectly mastered.

In fact, as described in more detail later, the product according to the invention can have a preventive effect on the aforementioned pathology. Administration of the protein or protein fragment before the inflammatory episode of the pathology makes it possible to obtain a decrease in inflammation and a swing of the immune response of the patient's body from a Th1-type response, characteristic of the pathology, to a type-Th2 response, during a flare-up of the disease. It is the change in the type of immune response observed after treatment with the protein and/or protein fragment according to the invention that makes it possible to treat preventively the chronic inflammatory diseases of various organs and even of diseases affecting an entire system, for example the nervous system. By "preventive treatment" is meant any treatment which, when administered before the inflammatory flare-up, makes it possible to suppress an inflammatory flare-up or reduce the intensity and/or duration of an inflammatory flare-up and/or that is capable of prolonging the length of time between two inflammatory flare-ups. The effect of the treatment can be evaluated from the inflammatory state of the organ or system in question.

By "therapeutic treatment" is meant any treatment which, when administered during an inflammatory flare-up, makes it possible to attenuate or suppress the flare-up, in particular one of the symptoms (in particular local inflammation, for example of the intestinal wall) connected with the flare-up.

As explained later, the product according to the invention acts by decreasing the secretion of specific interleukins of a Th1-type inflammatory response and/or increasing the production of interleukins corresponding to a type-Th2 immune response. These interleukins circulate throughout the body and their decrease or their increase potentially affects all organs.

It will be seen later that the product according to the invention allows the production of interleukins having a regulatory role (IL-10) in chronic inflammatory diseases connected with an immune system disorder generating a response of type Th1 and/or Th17. It was known that infestation with parasitic worms of the *Ascaris* genus in patients with multiple sclerosis reduces the progression of the disease (see "Association between parasite infection and immune responses in multiple sclerosis" Annals of Neurology 2007). However, nothing indicated that a specific protein of *Schistosoma* could have a therapeutic and/or preventive effect on a pathology affecting an organism's entire nervous system. It is therefore to the credit of the inventors that they tested the product according to the invention on a chronic inflammatory disease connected with an immune system disorder belonging to the neurological diseases and affecting the whole nervous system, such as, in particular, multiple sclerosis.

The patient for which the treatment is intended is not limited according to the invention. It may be an animal, a mammal, and more particularly a human being. It may also be a child. The Bilhvax project has in fact shown that the rSh28GST recombinant protein according to the invention is perfectly safe in children aged from 5 to 12 years. The products according to the invention may therefore be used for treating paediatric cases of chronic inflammatory diseases connected with an immune system disorder, and especially paediatric cases of these diseases. Thus, if there is a strong suspicion of a genetic factor causing said disease or making the patient more likely to develop the disease (in the case of a child if both parents had developed Crohn's disease, for example), the product according to the invention can be administered as a precaution.

Advantageously, the composition is administered at a dose of protein ranging from 50 μg/kg to 1000 μg/kg. The dose may be equal to 50 μg/kg, 500 μg/kg or 1000 μg/kg.

The concentration of purified protein administered per child is, for example, equal to 253 μg (which corresponds to a final dose of 100 μg of Bilhvax vaccine comprising rSh28GST28 plus aluminium hydroxide at a concentration of 1 mg/ml): the dose of protein may be, for example, greater than or equal to 100 μg and less than or equal to 500 μg of protein.

The method of administration of the composition of the invention is not limited according to the invention. The composition may be injected by the subcutaneous route or administered by the mucosal route, for example. The composition according to the invention may be administered, for example, in the form of a nasal or buccal spray, a suppository, a tablet, a lyophilizate, a capsule, a syrup, a solution injectable by the intravenous, subcutaneous or intramuscular route, an ointment or gel for topical application.

Figure 2:
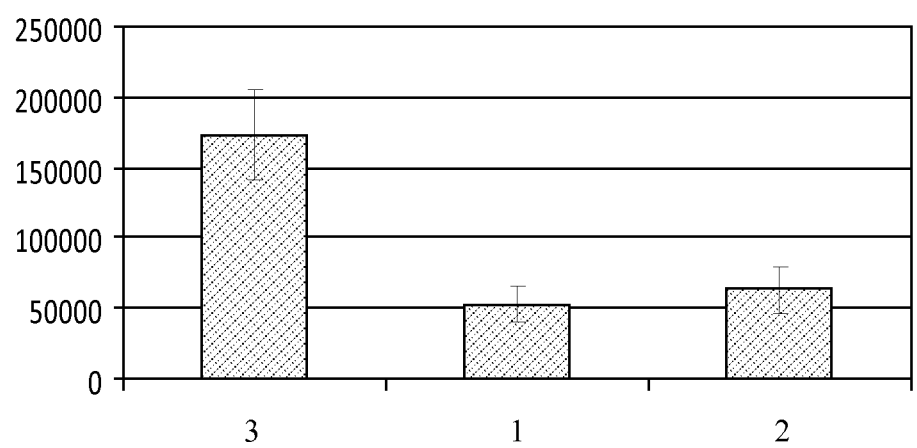
Figure 3:
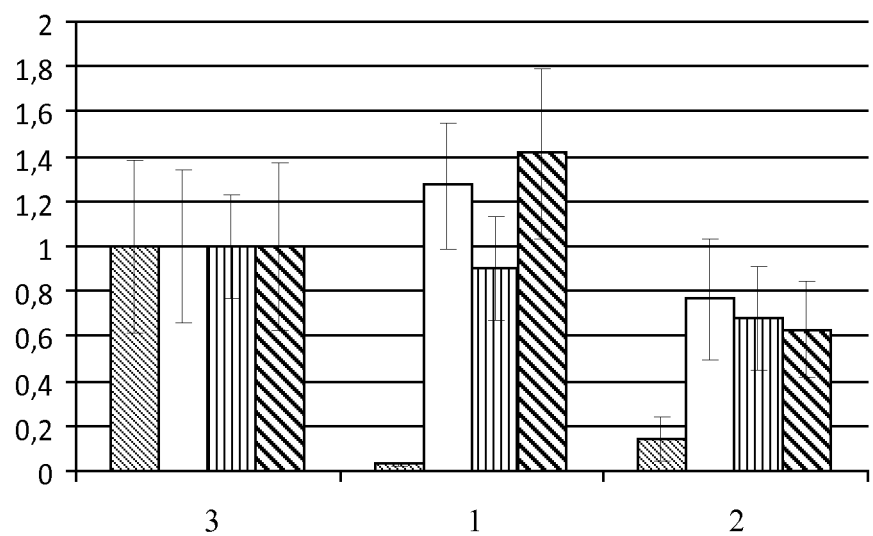
Figure 4:
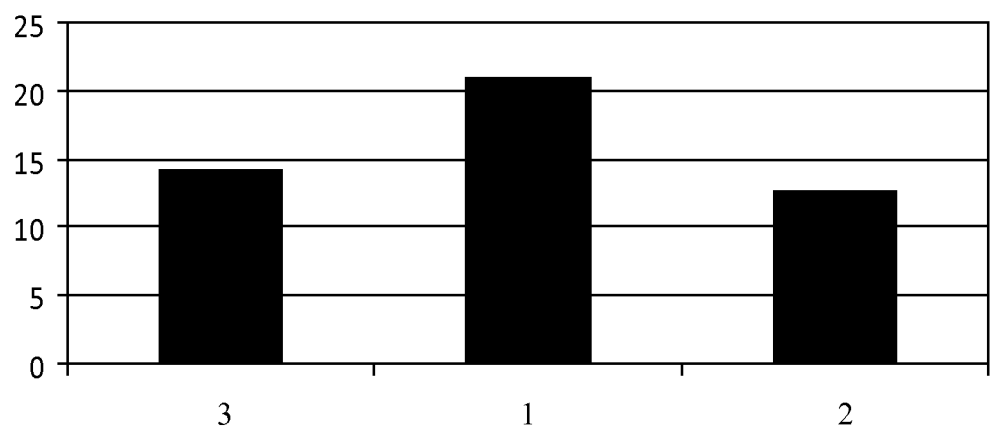
Figure 5:
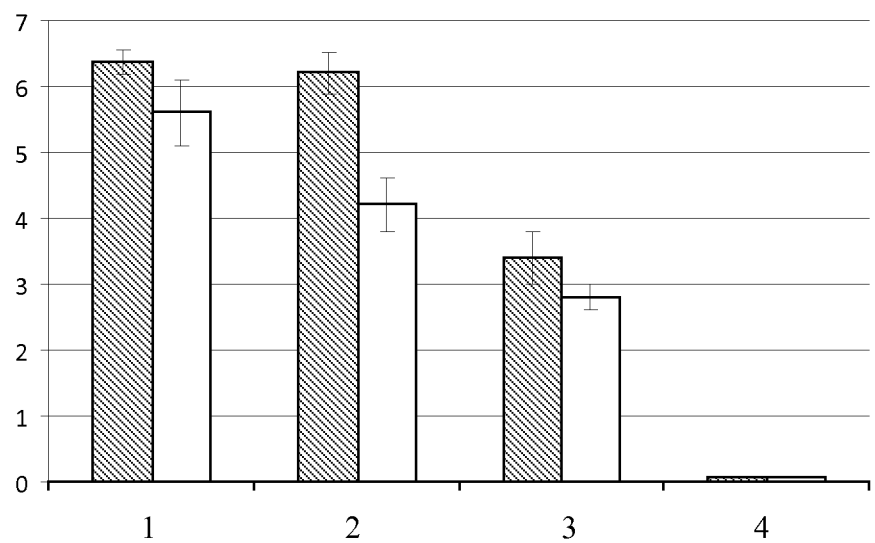
Figure 6:
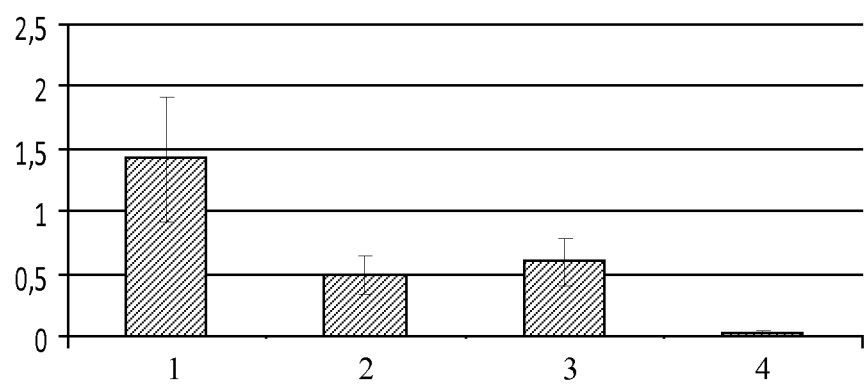
Figure 7:
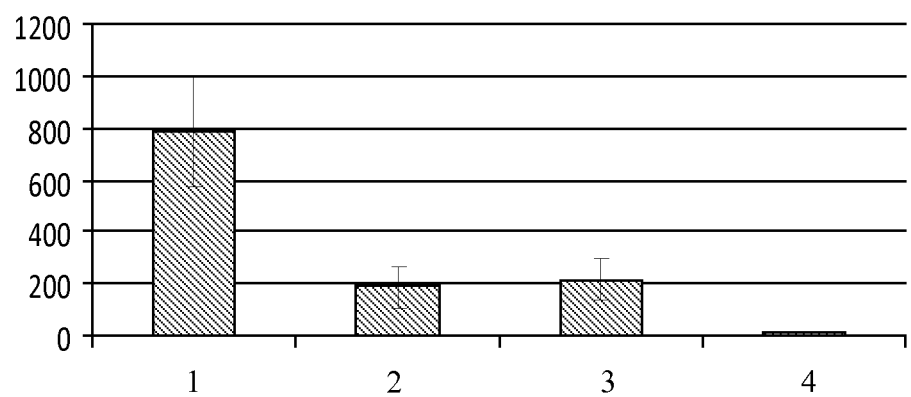
Figure 8:
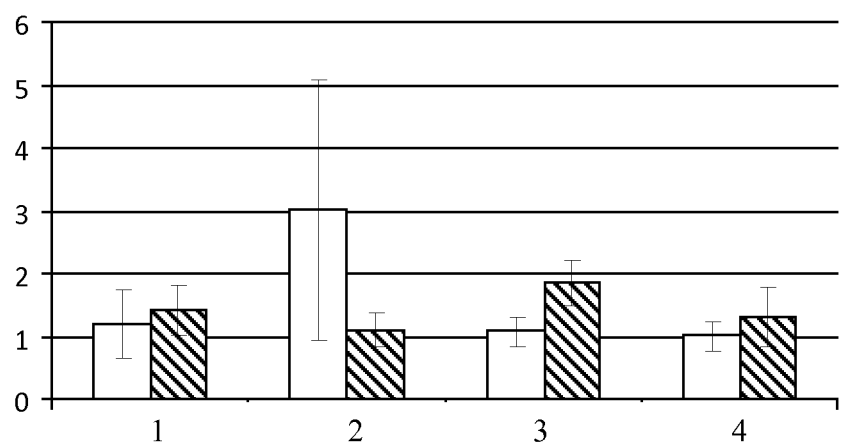
Figure 9:
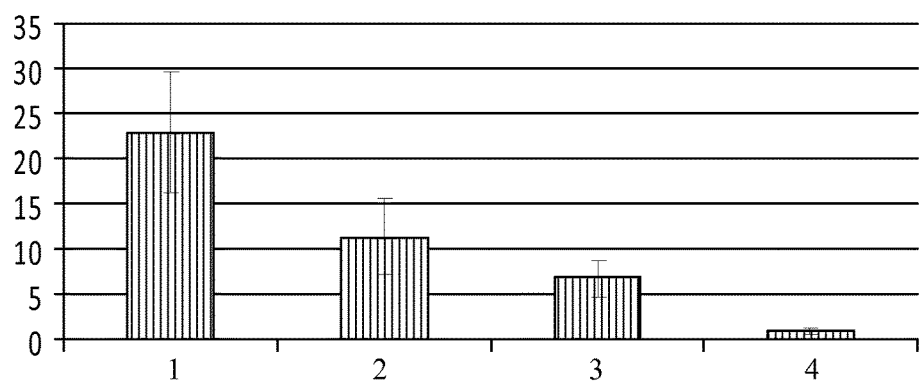
Figure 10:
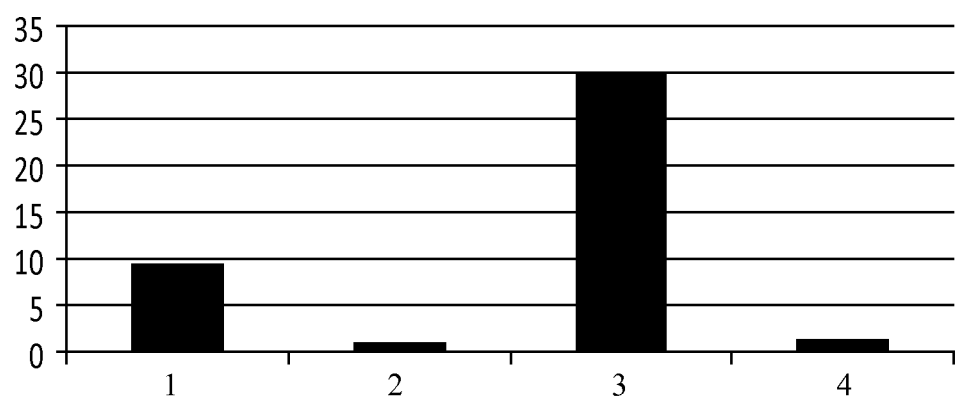
Figure 11:
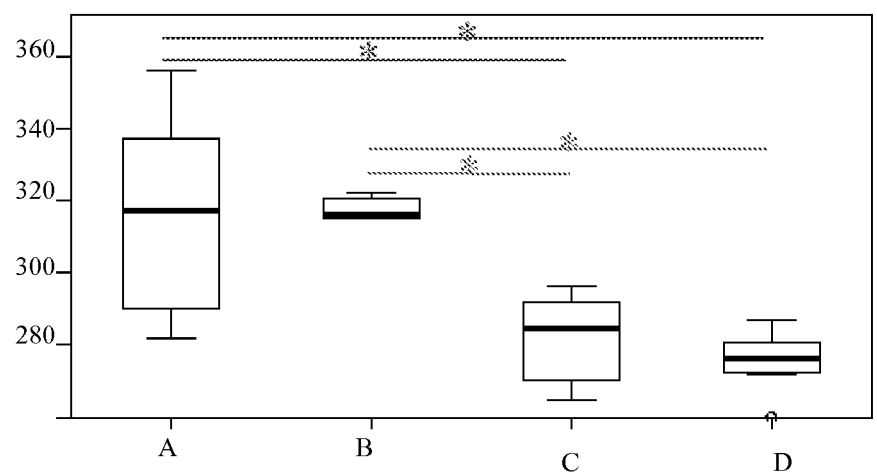
Figure 12:
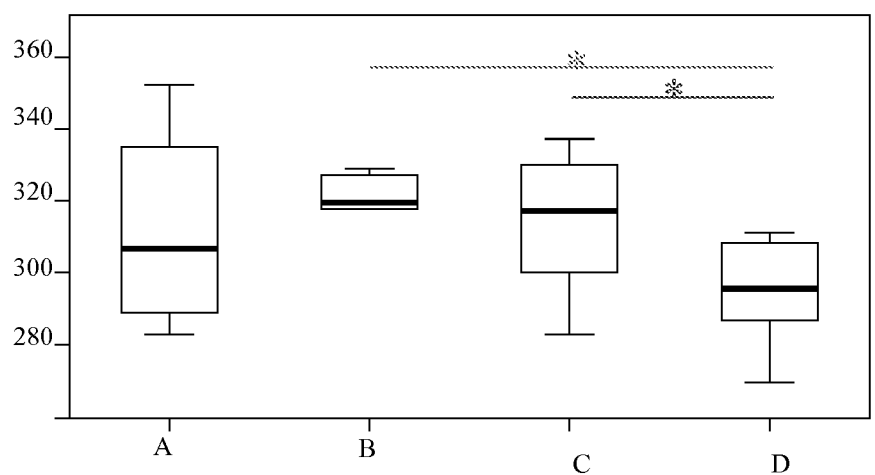
Figure 13:
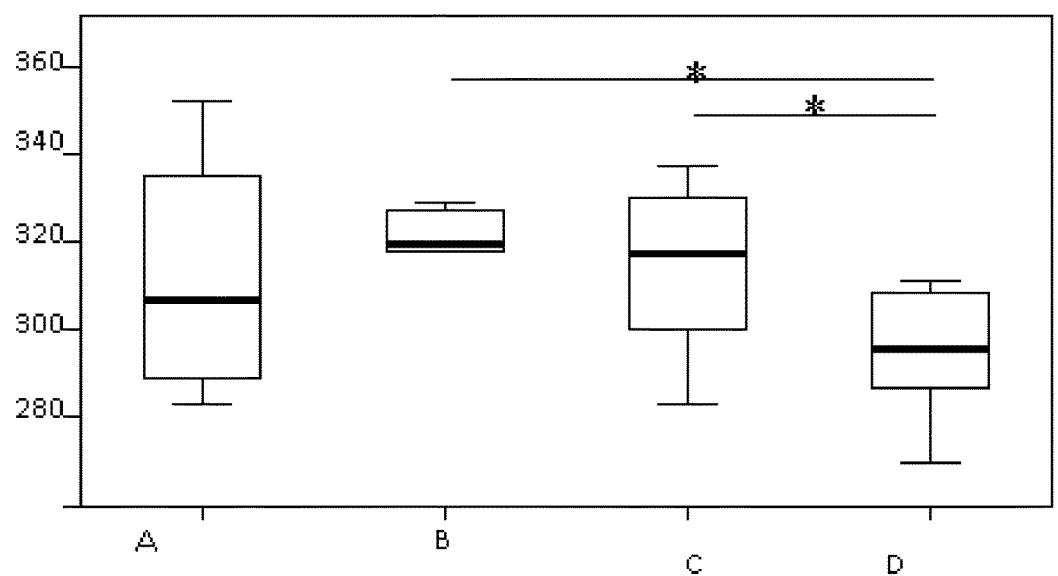
Figure 14:
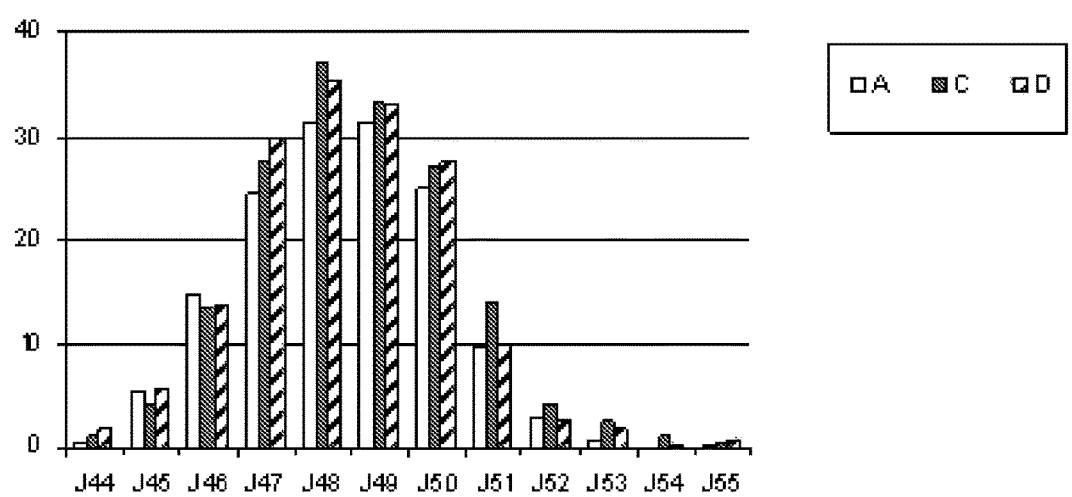

The present invention, its features and the various advantages that it provides will become apparent on reading the description given below and with reference to the examples, which are not limitative and to the attached figures, in which:

FIG. 1 shows the macroscopic and histological scores obtained for different groups of rats, group 1 being the group treated with the protein of the invention before the induction of colitis, group 2 being the group infected with *Schistosoma mansoni* before the induction of colitis with TNBS and group 3 being the control group. Group 1 is represented by the numeral 1 on the x-axis, group 2 is represented by the numeral 2 on the x-axis and group 3 is represented by the numeral 3 on the x-axis. The macroscopic score is represented by the column with diagonal hatching and the histological score is represented by the white column. The macroscopic and histological scores are quantified by the y-axis;

FIG. 2 shows the ratio of the level of myeloperoxidase (MPO) to the level of total proteins in the groups of rats mentioned with reference to FIG. 1, group 1 being represented by the numeral 1 on the x-axis, group 2 being represented by the numeral 2 on the x-axis and group 3 being represented by the numeral 3 on the x-axis. The y-axis shows the ratio of the level of MPO to the level of total proteins expressed in ng/mg;

FIG. 3 shows the quantity of messenger RNA coding for the interleukins IL-1b, IL-13, IL-5 and IL-10 in the same groups of rats as those used with reference to FIG. 1, group 1 being represented by the numeral 1 on the x-axis, group 2 being represented by the numeral 2 on the x-axis and group 3 being represented by the numeral 3 on the x-axis. The quantity of messenger RNA coding for interleukin IL-1 b is represented by the columns with fine diagonal hatching, the quantity of messenger RNA coding for interleukin IL-13 is represented by the columns with coarse diagonal hatching, the quantity of messenger RNA coding for interleukin IL-5 is represented by the white columns and the quantity of messenger RNA coding for interleukin IL-10 is represented by the columns with vertical hatching. The y-axis shows the quantities of messenger RNA in A.U.;

FIG. 4 shows the ratio of the level of messenger RNA coding for type I arginase (Arg) to the level of messenger RNA coding for inducible nitric oxide synthase (iNOS) in the same groups of rats as those used with reference to FIG. 1, group 1 being represented by the numeral 1 on the x-axis, group 2 being represented by the numeral 2 on the x-axis and group 3 being represented by the numeral 3 on the x-axis. The y-axis shows the ratio of the level of messenger RNA coding for type I arginase (Arg) to the level of messenger RNA coding for inducible nitric oxide synthase (iNOS);

FIG. 5 shows the macroscopic and histological scores obtained for different groups of mice, group 1 being the control group, group 2 being the group treated with 5-aminosalicylic acid before the induction of colitis, group 3 being the group treated with the protein according to the invention before the induction of colitis and group 4 being the group that receives an injection of ethanol before the induction of colitis. Group 1 is represented by the numeral 1 on the x-axis, group 2 is represented by the numeral 2 on the x-axis, group 3 is represented by the numeral 3 on the x-axis and group 4 is represented by the numeral 4 on the x-axis. The macroscopic score is represented by the columns with diagonal hatching and the histological score is represented by the white columns. The macroscopic and histological scores are quantified by the y-axis;

FIG. 6 shows the ratio of the level of myeloperoxidase to the level of total proteins in the groups of mice mentioned with reference to FIG. 5, group 1 being represented by the numeral 1 on the x-axis, group 2 being represented by the numeral 2 on the x-axis, group 3 being represented by the numeral 3 on the x-axis and group 4 being represented by the numeral 4 on the x-axis. The y-axis shows the ratio of the level of MPO to the level of total proteins expressed in ng/mg;

FIG. 7 shows the quantity of messenger RNA coding for interleukin IL-1 b in the same groups of mice as those used with reference to FIG. 5, group 1 is represented by the numeral 1 on the x-axis, group 2 is represented by the numeral 2 on the x-axis, group 3 is represented by the numeral 3 on the x-axis and group 4 is represented by the numeral 4 on the x-axis. The y-axis shows the quantity of messenger RNA in A.U.;

FIG. 8 shows the quantity of messenger RNA coding for the interleukins IL-5 and IL-13 in the same groups of mice as those used with reference to FIG. 5. Group 1 is represented by the numeral 1 on the x-axis, group 2 is represented by the numeral 2 on the x-axis, group 3 is represented by the numeral 3 on the x-axis and group 4 is represented by the numeral 4 on the x-axis. The quantity of messenger RNA coding for interleukin IL-5 is represented by the white columns and the quantity of messenger RNA coding for interleukin IL-13 is represented by the columns with diagonal hatching. The y-axis shows the quantity of messenger RNA in A.U.;

FIG. 9 shows the quantity of messenger RNA coding for interleukin IL-10 in the same groups of mice as those used with reference to FIG. 5. Group 1 is represented by the numeral 1 on the x-axis, group 2 is represented by the numeral 2 on the x-axis, group 3 is represented by the numeral 3 on the x-axis and group 4 is represented by the numeral 4 on the x-axis. The y-axis shows the quantity of messenger RNA in A.U.;

FIG. 10 shows the ratio of the level of messenger RNA coding for type I arginase to the level of messenger RNA coding for inducible nitric oxide synthase in the same groups of mice as those used with reference to FIG. 5. Group 1 is represented by the numeral 1 on the x-axis, group 2 is represented by the numeral 2 on the x-axis, group 3 is represented by the numeral 3 on the x-axis and group 4 is represented by the numeral 4 on the x-axis. The y-axis shows the ratio of the level of messenger RNA coding for type I arginase to the level of messenger RNA coding for inducible nitric oxide synthase;

FIG. 11 shows the analysis of the weights of the different groups of rats on D35 in the study of experimental allergic encephalitis (model of multiple sclerosis). Group A corresponds to the group of rats that received two injections of 5 μg/kg of rSh28GST in combination with aluminium hydroxide (alum) before the induction of EAE, it is represented on the x-axis by the letter A, group B corresponds to the group of rats that received two injections of 0.5 μg/kg of rSh28GST in combination with aluminium hydroxide (alum) before the induction of EAE, it is represented on the x-axis by the letter B, group C corresponds to the group of rats that received two injections of aluminium hydroxide alone before the induction of EAE, it is represented on the x-axis by the letter C, group D corresponds to the group of rats that did not receive any injection before the induction of EAE, it is represented on the x-axis by the letter D. The y-axis shows the weight of the rats in the different groups;

FIG. 12 shows the analysis of the weight (in g) of the different groups of rats mentioned with reference to FIG. 11, on D42, the reference letters of the groups are indicated on the x-axis whereas the weight of the rats is indicated on the y-axis;

FIG. 13 shows the analysis of the weight (in g) of the different groups of rats mentioned with reference to FIG. 11, on D48, the reference letters of the groups are indicated on the x-axis whereas the weight of the rats is indicated on the y-axis; and FIG. 14 shows the cumulative scores for the different groups of rats mentioned with reference to FIG. 11, the reference letters of the groups are indicated on the x-axis whereas the cumulative scores are indicated on the y-axis; with reference to FIG. 14, the rats in groups A and C received three injections, on D0, D14 and D28 respectively, of 5 μg/kg of rSh28GST in combination with aluminium hydroxide (alum) for group A and of alum alone for group C, before the induction of EAE on D35;

For FIGS. 11 to 13, the results are presented in the form of box-and-whisker plots. The Kruskal-Wallis and Mann- Whitney statistical tests were performed in order to determine the significant differences between the rats in the different groups. * P<0.05.

EXPERIMENTAL SECTION

Model of Crohn's Disease

Experimental Protocol of Colitis Induced in the Rat with TNBS (Model of Crohn's Disease)

The animals used are male Sprague Dawley rats (180 to 250 g). The animals are weighed and then food is withheld on the previous day so that they are fasting on the day of the induction of colitis. The rats are anaesthetized with pentobarbital (40 mg/kg) by intraperitoneal injection. 250 µl of a solution of TNBS (2,4,6-trinitrobenzene sulphonic acid) diluted in 100% ethanol (volume for volume) is injected intrarectally at a rate of 80 mg per kg of rat. The colitis is evaluated 96 h after injection of TNBS: the animals are weighed and sacrificed with an intracardiac injection of 300 µl of T61. The colon is removed for evaluating the macroscopic score. A transverse section of colon at 4 cm from the rectum is also taken and then pinned onto a piece of cork, on which it is immersed in a bath of 4% paraformaldehyde for 24 hours and then in a bath of 70% ethanol before dehydration and embedding in paraffin in order to for evaluate the histological score.

Experimental Protocol of Colitis Induced in the Mouse with TNBS (Model of Crohn's Disease)

The animals are male mice from the C57BL/6 gene pool. They are anaesthetized with a xylazine-ketamine mixture at a dose of 50 mg/kg each by the subcutaneous route. Colitis is induced intrarectally with 40 µl of solution of TNBS diluted in 100% ethanol (volume for volume) at a rate of 150 mg per kg of mouse. For the intrarectal injections of ethanol, it is 50% ethanol (control solvent).

Experimental Protocol of Infestation with *Schistosoma mansoni*

The rats are anaesthetized with a mixture of Valium (8 mg/kg) and ketamine (75 mg/kg) by intraperitoneal injection and then shaved on the abdomen. A solution containing 2000 cercariae (infective larvae) of *Schistosoma mansoni* is deposited on the animals' abdomens for 30 minutes; the cercariae penetrate transcutaneously. This infestation represents the "gold standard" of the experiment.

Protocol for the Investigation of rSh28GST in Multiple Sclerosis (Th1-Type Autoimmune Disease)

This model for investigating multiple sclerosis comprises the injection of an encephalitogenic peptide of myelin proteins (MBP) for the induction of an autoimmune disease, called EAE (experimental allergic encephalitis).

In order to demonstrate the preventive character of rSh28GST, 4-week-old Lewis rats are injected with a dose of 5 µg/kg of rSh28GST mixed with aluminium hydroxide (see paragraph "preparation of the test composition"). Four weeks later, EAE is induced (D=35). A clinical score is assessed on D=44 (first flare-up). The peak of EAE occurs on D=48. More or less complete recovery of the animal is observed on D=55. The animal's weight loss is measured throughout the protocol, a clinical score is recorded, the inflammatory infiltrates are quantified and the demyelination is measured at critical points (IHC).

Protocol for Showing the Curative Effect of rSh28GST in the Case of Multiple Sclerosis A rat model of EAE is used. Lewis rats are immunized with a composition of rSh28GST and aluminium hydroxide at the same time as the induction of EAE, optionally at critical points of the disease. The dose injected is equal to 5 µg/kg, 50 µg/kg, 500 µg/kg and 1000 µg/kg (these figures referring to the dose of rSh28GST, the concentration of aluminium hydroxide always being as indicated in the paragraph "preparation of the test composition"). The different cellular populations of interest are then analysed.

Protocol for Investigating Rheumatoid Arthritis (RA)

Two injections of collagen (auto-antigen) are performed intradermally at the base of the tail of the mice and the arthritis of the paw is measured after 21 days according to a conventional score. The immunological parameters (antibodies, cytokines, regulatory cells) are then monitored.

In order to determine the preventive effect, a dose of 1000 µg/kg of rSh28GST mixed with aluminium hydroxide (see paragraph "preparation of the test composition") is injected before the two injections of collagen. In order to demonstrate the therapeutic effect, the test composition (1000 µg/kg for rSh28GST protein) is injected at the same time as the aforementioned two injections of collagen.

Assay of Myeloperoxidase (MPO)

The level of myeloperoxidase contained in the colic tissues is evaluated by the immunological technique of the Sandwich ELISA ("Enzyme-Linked ImmunoSorbent Assay") type and is referred to the level of proteins contained in this same colic tissue.

The colic tissue (containing MPO in the case of inflammation) is first ground in order to obtain a homogenizate thereof. The latter is deposited in a well of the plate already coated with an anti-MPO antibody. The antigen (here MPO)-anti-MPO antibody reaction is then carried out. A second antibody directed against the MPO molecule and labelled with biotin is then added and is revealed by adding streptavidin (having high affinity for the biotin) coupled to a chromogen. In the presence of its substrate, the latter releases a coloured substance, the optical density of which is evaluated with a spectrophotometer. The measured optical density is proportional to the quantity of MPO protein contained in the colic tissue homogenizate.

Preparation of the Test Composition (rSh28GST Protein+Aluminium Hydroxide)

The rSh28GST protein used is the recombinant protein produced in *Saccharomyces cerevisiae* and manufactured by the company Eurogentec. The complete sequence of the gene represented by the sequence SEQ ID NO: 4 is used. The protein is in lyophilized form, one vial contains 165 µg (+ or −5%) of proteins. The pharmaceutical composition is reconstituted with 660 µl of aluminium hydroxide gel (2%) diluted to a 10th in physiological saline solution in one vial of protein, hence a concentration of 250 µg/ml. The animals are injected subcutaneously with the composition thus obtained at the same concentration. It is this mixture of rSh28GST+aluminium hydroxide that is injected into the animals in all the experimental protocols. The doses indicated correspond to the dose of rSh28GST protein.

"Arginase I/Nitric Oxide Synthase 2" Ratio

The ratio represents the level of messenger RNA coding for arginase I (Arg) to the level of messenger RNA coding for inducible nitric oxide synthase (iNOS) of type 2 for a given colic sample. The level of messenger RNA is obtained by a real-time polymerase chain reaction (RT-PCR) technique. This is a technique in molecular biology for the in-vitro amplification of DNA. At each amplification cycle, the total quantity of DNA is measured by means of a fluorescent probe; a quantification of the initial messenger RNA can be obtained from the kinetics of all of the amplification cycles.

Expression of the Messenger RNA of Interleukins IL-1 b, IL-13, IL-5 and IL-10

The presence and quantification of the messenger RNA of different interleukins in the colic tissues are obtained using the real-time PCR technique explained in the preceding paragraph.

Experimental Results in the Rat

Three groups of Sprague Dawley rats are formed. Group 1 receives 2 subcutaneous injections of a composition as mentioned above (rSh28GST+aluminium hydroxide) at a dose of 50 µg/kg (for rSh28GST protein), the first on D=0 and the second on D=28. Group 2 ("gold standard") is infested with 2000 cercariae of Schistosoma mansoni on D=0. Group 3 is the control group. On D=35, colitis is induced in the rats in the three groups by intrarectal injection of TNBS, then the rats are sacrificed on D=39.

Macroscopic and Histological Scores

As shown in FIG. 1, it is found that the inflammation of the intestinal wall of the rats in groups 1 and 2 is decreased relative to that of the rats in group 3. Moreover, the histological score confirms the macroscopic score.

Assay of Myeloperoxidase (MPO)

Myeloperoxidase is an enzyme present in the neutrophilic granulocytes as well as a marker of inflammation. As shown in FIG. 2, it is noted that the quantity of MPO in the colic tissues of the rats in group 1 and in group 2 is reduced relative to the quantity present in the colic tissues of the rats in group 3. These results show that the injection of the rSh28GST protein allows a significant reduction in the secretion of MPO in inflammatory colitis.

Interleukins IL-1b, IL-13, IL-5 and IL-10

IL-1b is an interleukin secreted during a Th1-type inflammatory immune response. As shown in FIG. 3, it can be seen that the quantity of messenger RNA coding for this interleukin is reduced in the colic tissues of the rats in groups 1 and 2 (even more in group 1 than in group 2). These results show that the injection of the rSh28GST protein causes a more pronounced reduction in the Th1-type immune response than the infection by Schistosoma mansoni on D0. Interleukins IL-5 and IL-13 are secreted during a type-Th2 immune response. As shown in FIG. 3, the quantity of messenger RNA coding for these two interleukins is increased in the colic tissues of the rats in group 1 relative to the tissues of the rats in group 3. The quantity of messenger RNA coding for IL-5 and for IL-13 is greater in group 1 than in group 2. These results show that the rSh28GST protein induces a strong expression of the messenger RNA of IL-5 and IL-13. The RSh28GST protein therefore makes it possible to induce a type-Th2 immune response that counterbalances the Th1-type immune response found in the case of colitis induced with TNBS.

It has been demonstrated that patients suffering from Crohn's disease react favourably to treatment based on interleukin 10 (see Braat H, Rottiers P, Hommes D W, Huyghebaert N, Remaut E, Remon J P, van Deventer S J, Neiryncjk S, Peppenlenbosch M P, Steidler L (June 2006) "A phase I trial with transgenic bacteria expressing Interleukin-10 in Crohn's disease" Clin. Gastroenterol. Hepatol. 4 (6): 754-9. doi: 10.1016/j.cgh.2006.03.028. PMID 16716759). As shown in FIG. 3, more messenger RNA coding for IL-10 is present in the colic tissues of the rats in group 1 than of the rats in group 2. These results show that the rSh28GST protein induces the production of messenger RNA coding for IL-10, which is a favourable factor in the case of the therapeutic treatment of Crohn's disease. Moreover, IL-10 is secreted during a type-Th2 immune response, which is in agreement with the results illustrated in FIG. 3.

"Arginase I/Nitric Oxide Synthase 2" Ratio

Type I arginase is an enzyme, used here as a marker, which characterizes the so-called alternative M2 macrophages, present in Th1 anti-inflammatory immune reactions; type 2 nitric oxide synthase is also an enzyme, but is used as a marker characterizing the so-called conventional macrophages present in Th2 pro-inflammatory immune reactions. The ratio of these two enzymes reflects the presence of macrophages of a particular type in the colic tissues, and makes it possible to assess the balance between the two immune responses Th1 and Th2.

As shown in FIG. 4, the rSh28GST protein can promote the type-Th2 response, which will thus counterbalance the Th1-type response induced by colitis.

Experimental Results in the Mouse

The two rodent models used (rats and mice) are classical experimental models that are widely described in the literature as models of Crohn's disease. The mouse strain used here (C57 BL6) is rather pro-Th1 and therefore obtaining results with a decrease in Th1-type response in this animal model is even more convincing than in the rat.

Four groups of mice are formed. Group 1 receives no treatment, only colitis induced with TNBS on D=35: this is the control group. The mice in group 2 are fed starting from D=30 with pellets containing 5-ASA: 5-aminosalicylic acid at a rate of 1 g of 5-ASA per 600 g of pellets, then colitis is induced with TNBS on D=35. The mice in group 3 receive two injections of the composition as mentioned above (rSh28GST+aluminium hydroxide) at a dose of 1000 µg/kg (for rSh28GST) on D0 and D28, and then an intrarectal injection of TNBS. The mice in group 4 only receive an intrarectal injection of 50% ethanol on D35 (TNBS control solvent). The mice in the four groups are sacrificed on D=37.

Macroscopic and Histological Score

As shown in FIG. 5, the macroscopic score that reflects inflammation is greatly reduced in the mice in group 3. The results obtained are better than those obtained with 5-ASA. The histological score confirms the macroscopic score.

Assay of Myeloperoxidase (MPO)

FIG. 6 shows that rSh28GST reduces, in the case of colitis, the level of MPO in the colic tissues of the mice in group 3. In the case when the mice did not receive colitis (group 4), the MPO activity is unchanged.

Interleukins IL-1b, IL-13, IL-5 and IL-10

FIGS. 7 to 9 confirm, in the mouse, the results obtained in the rat. The rSh28GST protein reduces the level of messenger RNA coding for IL-1b and increases that of IL-13 and IL-5 in the case of colitis. The aforementioned protein therefore seems to have a preventive effect owing to the increase in production of IL-10.

"Type I Arginase/Nitric Oxide Synthase 2" Ratio

FIG. 10 shows, as in the case of the rat, an increase in the ratio of the level of messenger RNA coding for type I arginase to that coding for nitric oxide synthase 2 in the case of group 3 relative to groups 1, 2 and 4. This increase in the "Type I Arginase/Nitric Oxide Synthase 2" ratio is suggestive of an increase in the presence of macrophages associated with a Th2 response. The composition of the invention can therefore promote a type-Th2 response in the case of induced colitis, which is not the case for 5-aminosalicylic acid (see group 2).

Moreover, another group of mice received the two injections of rSh28GST as mentioned above and a single intrarectal injection of ethanol instead of TNBS. This tests the influence of the protein without inflammation. In this group, the results for which are not shown in the figures, MPO activity is unchanged. The protein of the invention therefore reduces inflammation but does not alter the levels of MPO when there is no induced inflammation. The results for this group also show that, without induced inflammation, the protein alone makes it possible to increase the messenger RNA coding for IL-13, IL-5 and the IL-10 and that without induced inflammation, the protein shows no activity on the macrophages.

Model of Multiple Sclerosis

The model used is the model of experimental allergic encephalitis (EAE). In the present case, EAE is induced by an injection of myelin basic protein (MBP). The effect of immunization with rSh28GST on the development of EAE induced with MBP in a Lewis rat model was investigated.

Materials and Methods:

1—Reagents:
 a) Preparation of rSh28GST(alum): (Batch: GLP. Designated: L-Bix-P08/165a). The term "alum" denotes an aqueous suspension of aluminium hydroxide as described in more detail below.
  Dose of 5 µg/kg (+alum):
  1 vial containing 165 µg of rSh28GST is dissolved in 660 µl of physiological saline solution in order to obtain a solution of 250 µg/ml. A solution is then prepared at 10 µg/ml: dilution to 1:25 in physiological saline solution. Alum is added: 10 µl ("alum" denotes alhydrogel 2% VacciGrade_50 ml cat: vac-alu-50 batch: AHG-33-427)
  Dose of 0.5 µg/kg (+alum):
  Starting from the solution of rSh28GST at 250 µg/ml, a solution is prepared at 1 µg/ml: dilution to 1:250 in physiological saline solution. Alum is added: 10 µl (alum denotes alhydrogel 2% VacciGrade_50 ml cat: vac-alu-50 batch: AHG-33-427)
 b) Alum dose:
  The alum dose is obtained by diluting 10 µl of alum with 2.5 ml of physiological saline solution (alum denotes alhydrogel 2% VacciGrade_50 ml cat: vac-alu-50 batch: AHG-33-427)
 c) Preparation of the emulsion intended for inducing EAE
  A solution is prepared at 100 µg/ml, i.e. 3 ml of CFA at 2 mg/ml+1 ml of IFA+4 ml of MBP solution at 200 µg/ml in SPB. Two 8-ml doses equivalent to 50 µl/5 µg of MBP are injected in the rat's paws. In total, 100 µl/10 µg MBP is injected per rat.
  The aforementioned solution of MBP in SPB is obtained by diluting MBP (batch 2011): 1064 µl at 940 µg/ml in 3.94 ml of sodium perborate (SPB).
  CFA denotes complete Freund adjuvant, i.e. comprising mycobacteria (*M. tuberculosis*). IFA denotes incomplete Freund adjuvant. 1 mL of incomplete Freund adjuvant consists of 0.85 mL of paraffin oil and 0.15 mL of mannide monooleate. In its complete form, it further comprises a given quantity of *Mycobacterium tuberculosis* (H37Ra, ATCC 25177), thermally inactivated (killed thermally) and dried.
  CFA at 2 mg/ml of *M. tuberculosis*: IFA Sigma (ref. F5506 batch: 070M8706) and *Mycobacterium tuberculosis* H37 RA Difco (ref. 3114-25 batch. 131582 L-00535-02) so as to obtain the aforementioned concentration of 2 mg/ml.
  Anaesthetics supplied by the animal husbandry section: ketamine and xylazine
 d. Animals:
  Male Lewis rats aged 6 weeks (CERJ Janvier breeding station) at the start of the experiments and immunized with MBP at 12 weeks (n=10 rats/group). The injections are performed subcutaneously in the rat's neck. 40 rats were used.

Experimental Protocol

The experiments begin when the rats reach seven weeks of age.

On D=0 the 10 rats in group A receive an injection of the aforementioned solution containing 5 µg/kg of rSh28GST and alum. On D=0 the 10 rats in group B receive an injection of the aforementioned solution containing 0.5 µg/kg of rSh28GST and alum. On D=0 the 10 rats in group C receive an injection of the aforementioned alum solution only; they receive a second injection of alum only on D=28. On D=0 the 10 rats in group D, which is the control group, do not receive any injection. On D=28, the rats in groups A and B receive a 2nd injection of rSh28GST(alum) at the same dosage as the first injection On D=35, EAE is induced with an injection containing myelin base protein (see paragraph c)). The clinical study begins on D44 and ends on D56 with sacrifice of the animals.

Humoral Response of the Rats Immunized with P28 GST

Assay of the anti-rSh28GST IgG antibodies was carried out on the blood samples taken on D35 (day of the induction of EAE) and D56 (day of sacrifice) by the ELISA technique. The results reveal that only 6 rats (out of 10) in group A and 4 rats (out of 10) in group B presented a detectable immune response throughout the clinical protocol. Only these rats presenting an immune response in the form of detectable production of anti-rSh28GST IgG antibodies to rSh28GST on D35 and on D56 were included in the next study concerning the weights of the rats.

Investigation of the Variations of the Weight of the Rats in the Four Groups

The animals' weight was evaluated on the day of the induction of EAE (i.e. 35 days after the first injection of rSh28GST and every day starting from the first symptoms (D42). The results obtained indicate that a weight loss of about 10% for all the groups is observed when the disease reaches its peak.

However, non-parametric statistical tests were performed on these data and revealed significant differences between the groups.

Thus, on D35, the rats in groups A and B (whatever the dose of P28GST) have a significantly higher weight relative to the rats in groups C and D.

These results can be seen in FIG. 11, which shows the analysis of the weights of the different groups of rats on D35. The results are presented in the form of box-and-whisker plots. The Kruskal-Wallis and Mann-Whitney statistical tests were carried out in order to determine the significant differences between the rats in the different groups. * $P<0.05$.

Moreover, it appears that on D42 and on D48, the sick rats in group D have a lower body weight than the rats in groups A and B.

FIG. 12 shows the analysis of the weights of the different groups of rats on D42. FIG. 13 shows the analysis of the weights of the different groups of rats on D48. For both figures, the results are presented in the form of box-and-whisker plots. The Kruskal-Wallis and Mann-Whitney statistical tests were used in order to determine the significant differences between the rats that received 2 doses of rSh28GST(alum) at 5 µg/kg, 0.5 µg/kg, alum alone and control. * $P<0.05$.

Clinical Scores

For the evaluation of the clinical score, other groups of rats were used (n=22 for group A, n=24 for group C and n=8 for group D). The protocol is the same as the aforementioned except that the rats in group A received three injections (respectively on D0, D14 and D28) of 5 μg/kg of rSh28GST in combination with aluminium hydroxide (alum) (so as to obtain an immune response) and the rats in group C received three injections (on D0, D14 and D28) of alum alone. EAE was induced on D35. The rats were scored daily starting from the first symptoms (D44) up to the end of the remission phase (D55). Clinical scores were assigned according to the following reference scale: score of 0=no symptom; score of 0.5=muscular weakness in the tail; score of 1=hypotonic tail; score of 2=hypotonic tail+muscular weakness in the hind limbs; score of 3=1 hind limb paralysed; score of 4=both hind limbs paralysed, score of 5=both hind limbs paralysed+unable to clean itself and score of 6=death of the animal. Thus, FIG. 14 shows the cumulative scores observed for the aforementioned different groups of rats as a function of time post-immunization with rSh28GST. The groups are shown on the x-axis and the cumulative score is shown on the y-axis. The rats in group A begin the flare-up on D44 with a peak reached on D46 following the same kinetics as groups C and D but the cumulative scores starting from D45 are lower than those of groups C and D, in particular between D45 and D55. The decreases in the cumulative score are significant on D45 and D48. The rats that developed an antibody response at a dose of 5 μg/kg (group A) therefore display a decrease in the cumulative clinical scores. Moreover, the mortality in group A is zero, whereas one rat in the control group D died, as well as three rats in group C (alum alone).

The invention claimed is:

1. A method of preventing and/or therapeutically treating a chronic inflammatory disease connected with an immune system disorder generating an immune response of type Th1/Th17, comprising administering to a subject in need thereof an effective amount of a product consisting of a protein, thereby leading to the induction of a Th2 response and/or the decrease of the Th1 response, wherein: said protein comprises or is constituted by the 28 kDa glutathione S-transferase protein from a schistosome selected from the group consisting of *Schistosoma haematobium, Schistosoma mansoni*, and *Schistosoma bovis* represented by the sequences SEQ ID NO: 1, SEQ ID NO: 2, and SEQ ID NO: 3, respectively.

2. The method according to claim 1, wherein said protein is represented by the sequence SEQ ID NO: 1.

3. The method according to claim 2, wherein the product is the expression product of a nucleotide sequence coding for the 28 kDa glutathione-S-transferase protein represented by SEQ ID NO: 1.

4. The method according to claim 3, wherein the product is the expression product of said coding sequence SEQ ID NO: 4 in *Saccharomyces cerevisiae* or in *Escherichia coli*.

5. The method according to claim 1, wherein, said disease is selected from the autoimmune inflammatory diseases consisting of Berger's disease, Basedow's disease, Hashimoto's thyroiditis, primary myxoedema, coeliac disease, ulcerative colitis, Crohn's disease, rheumatoid arthritis, primary biliary cirrhosis, primary sclerosing cholangitis, autoimmune haemolytic anaemias, Biermer's anaemia (pernicious anaemia), lupus erythematosus, CREST syndrome, type 1 diabetes, scleroderma, pemphigus vulgaris, bullous pemphigoid, acquired epidermolysis bullosa, dermatitis herpetiformis, myasthenia, Lambert-Eaton myasthenic syndrome, polymyositis, Goujerot-Sjögren syndrome, multiple sclerosis, rheumatoid arthritis, Graves' disease and psoriasis.

6. The method according to claim 1, wherein the subject is a child.

7. The method according to claim 1, wherein, a pharmaceutical composition is administered, said pharmaceutical composition comprising, as active ingredient, said product and a pharmacologically acceptable excipient.

8. The method according to claim 7, a wherein the pharmaceutical composition prevents and/or therapeutically treats an autoimmune inflammatory disease selected from the group consisting of: Berger's disease, Basedow's disease, Hashimoto's thyroiditis, primary myxoedema, coeliac disease, ulcerative colitis, Crohn's disease, rheumatoid arthritis, primary biliary cirrhosis, primary sclerosing cholangitis, autoimmune haemolytic anaemias, Biermer's anaemia (pernicious anaemia), lupus erythematosus, CREST syndrome, type 1 diabetes, scleroderma, pemphigus vulgaris, bullous pemphigoid, acquired epidermolysis bullosa, dermatitis herpetiformis, myasthenia, Lambert-Eaton myasthenic syndrome, polymyositis, Goujerot-Sjögren syndrome, multiple sclerosis, rheumatoid arthritis, Graves' disease and psoriasis and the possible paediatric forms of these diseases.

9. The method according to claim 1, wherein the pharmaceutical composition further comprises an adjuvant selected from the aluminium salts or aluminium hydroxide.

10. The method according to claim 9, wherein the concentration of adjuvant in the pharmaceutical composition is selected from the group consisting of from 0.5 mg/ml to 2 mg/ml, from 0.3 mg/ml to 1 mg/ml, from 220 µg/ml to 280 µg/ml, and approximately equal to 250 µg/ml.

* * * * *

SEQUENCE LISTING

```
<160> NUMBER OF SEQ ID NOS: 6

<210> SEQ ID NO 1
<211> LENGTH: 212
<212> TYPE: PRT
<213> ORGANISM: Schistosoma haematobium

<400> SEQUENCE: 1

Met Met Thr Gly Asp His Ile Lys Val Ile Tyr Phe Asn Gly Arg Gly
1               5                   10                  15

Arg Ala Glu Ser Ile Arg Met Thr Leu Val Ala Ala Gly Val Asn Tyr
                20                  25                  30

Glu Asp Glu Arg Ile Ser Phe Gln Asp Trp Pro Lys Ile Lys Pro Thr
            35                  40                  45

Ile Pro Gly Gly Arg Leu Pro Ala Val Lys Ile Thr Asp Asn His Gly
        50                  55                  60

His Val Lys Trp Met Val Glu Ser Leu Ala Ile Ala Arg Tyr Met Ala
65                  70                  75                  80

Lys Lys His His Met Met Gly Gly Thr Glu Glu Tyr Tyr Asn Val
                85                  90                  95

Glu Lys Leu Ile Gly Gln Ala Glu Asp Leu Glu His Glu Tyr Tyr Lys
            100                 105                 110

Thr Leu Met Lys Pro Glu Glu Glu Lys Gln Lys Ile Ile Lys Glu Ile
        115                 120                 125

Leu Asn Gly Lys Val Pro Val Leu Leu Asp Ile Ile Cys Glu Ser Leu
    130                 135                 140

Lys Ala Ser Thr Gly Lys Leu Ala Val Gly Asp Lys Val Thr Leu Ala
145                 150                 155                 160

Asp Leu Val Leu Ile Ala Val Ile Asp His Val Thr Asp Leu Asp Lys
                165                 170                 175

Glu Phe Leu Thr Gly Lys Tyr Pro Glu Ile His Lys His Arg Glu Asn
            180                 185                 190

Leu Leu Ala Ser Ser Pro Arg Leu Ala Lys Tyr Leu Ser Asp Arg Ala
        195                 200                 205

Ala Thr Pro Phe
    210

<210> SEQ ID NO 2
<211> LENGTH: 211
<212> TYPE: PRT
<213> ORGANISM: Schistosoma mansoni

<400> SEQUENCE: 2

Met Ala Gly Glu His Ile Lys Val Ile Tyr Phe Asp Gly Arg Gly Arg
```

```
               1               5                    10                    15
            Ala Glu Ser Ile Arg Met Thr Leu Val Ala Ala Gly Val Asp Tyr Glu
                            20                    25                    30

Asp Glu Arg Ile Ser Phe Gln Asp Trp Pro Lys Ile Lys Pro Thr Ile
                            35                    40                    45

Pro Gly Gly Arg Leu Pro Ala Val Lys Val Thr Asp His Gly His
                        50                    55                    60

Val Lys Trp Met Leu Glu Ser Leu Ala Ile Ala Arg Tyr Met Ala Lys
             65                    70                    75                    80

Lys His His Met Met Gly Glu Thr Asp Glu Glu Tyr Tyr Ser Val Glu
                                85                    90                    95

Lys Leu Ile Gly Gln Ala Glu Asp Val Glu His Glu Tyr His Lys Thr
                        100                   105                   110

Leu Met Lys Pro Gln Glu Glu Lys Glu Lys Ile Thr Lys Glu Ile Leu
                        115                   120                   125

Asn Gly Lys Val Pro Val Leu Leu Asn Met Ile Cys Glu Ser Leu Lys
                        130                   135                   140

Gly Ser Thr Gly Lys Leu Ala Val Gly Asp Lys Val Thr Leu Ala Asp
            145                   150                   155                   160

Leu Val Leu Ile Ala Val Ile Asp His Val Thr Asp Leu Asp Lys Gly
                                165                   170                   175

Phe Leu Thr Gly Lys Tyr Pro Glu Ile His Lys His Arg Glu Asn Leu
                        180                   185                   190

Leu Ala Ser Ser Pro Arg Leu Ala Lys Tyr Leu Ser Asn Arg Pro Ala
                        195                   200                   205

Thr Pro Phe
                210

<210> SEQ ID NO 3
<211> LENGTH: 211
<212> TYPE: PRT
<213> ORGANISM: Schistosoma bovis

<400> SEQUENCE: 3

Met Thr Gly Asp His Ile Lys Val Ile Tyr Phe Asn Gly Arg Gly Arg
             1               5                    10                    15

Ala Glu Ser Ile Arg Met Thr Leu Val Ala Ala Gly Val Asn Tyr Glu
                            20                    25                    30

Asp Glu Arg Ile Ser Phe Gln Asp Trp Pro Lys Ile Lys Pro Thr Ile
                            35                    40                    45

Pro Gly Gly Arg Leu Pro Ala Val Lys Ile Thr Asp Asn His Gly His
                        50                    55                    60

Val Lys Trp Met Leu Glu Ser Leu Ala Ile Ala Arg Tyr Met Ala Lys
             65                    70                    75                    80

Lys His His Met Met Gly Glu Thr Asp Glu Glu Tyr Tyr Asn Val Glu
                                85                    90                    95

Lys Leu Ile Gly Gln Val Glu Asp Leu Glu His Glu Tyr His Lys Thr
                        100                   105                   110

Leu Met Lys Pro Glu Glu Glu Lys Gln Lys Ile Thr Lys Glu Ile Leu
                        115                   120                   125

Asn Gly Lys Val Pro Val Leu Leu Asp Ile Ile Cys Glu Ser Leu Lys
                        130                   135                   140

Ala Ser Thr Gly Lys Leu Ala Val Gly Asp Lys Val Thr Leu Ala Asp
            145                   150                   155                   160
```

Leu Val Leu Ile Ala Val Ile Asp His Val Thr Asp Leu Asp Lys Glu
            165                 170                 175

Phe Leu Thr Gly Lys Tyr Pro Glu Ile His Lys His Arg Glu Asn Leu
        180                 185                 190

Leu Ala Ser Ser Pro Arg Leu Ala Lys Tyr Leu Ser Asp Arg Ala Ala
            195                 200                 205

Thr Pro Phe
    210

<210> SEQ ID NO 4
<211> LENGTH: 803
<212> TYPE: DNA
<213> ORGANISM: Schistosoma haematobium

<400> SEQUENCE: 4
tctgtctgac tgtatgatga ctggtgatca tatcaaggtt atctatttta acggacgcgg      60
acgagctgaa tcgatccgga tgacacttgt ggcagctggt gtgaactacg aagatgagag     120
aattagtttc caagattggc cgaaaatcaa accaactatt ccgggcggac gattgcctgc     180
agtgaaaatc accgataatc atgggcacgt gaaatggatg gtagagagtt ggctattgc     240 acggtatatg gcgaagaagc atcatatgat gggaggaaca gaagaggagt attataatgt     300
tgagaagttg attggtcagg ctgaagatct agaacatgaa tattacaaaa ctttgatgaa     360
gccagaagaa gagaaacaga gataatcaa agagatactg aacggcaaag taccagttct     420
tctcgatatt atctgcgaat ctctgaaagc gtccacaggc aagctggctg ttggggataa     480
agtgactcta gccgacttag ttctgattgc tgtcattgac catgtgactg atctggataa     540
agaatttcta actggcaagt atcctgagat ccataaacat agagaaaatc tactagccag     600
ttcaccgaga ttggcgaaat atttatcaga cagggctgca actccottct agaactgtca     660 acagaatgct gggtgtgacg agattgaaga tactgatagt agtgcactgg tgcgaccttt     720
ttactaagac gtcatttgtt ttatggtatt ttttttcgca atcgttatta aaataaactt     780
agttttctgt ttaaaaaaaa aaa                                             803

<210> SEQ ID NO 5
<211> LENGTH: 211
<212> TYPE: PRT
<213> ORGANISM: Schistosoma japonicum

<400> SEQUENCE: 5

Met Ala Cys Gly His Val Lys Leu Ile Tyr Phe Asn Gly Arg Gly Arg
1               5                   10                  15

Ala Glu Pro Ile Arg Met Ile Leu Val Ala Ala Gly Val Glu Phe Glu
            20                  25                  30

Asp Glu Arg Ile Glu Phe Gln Asp Trp Pro Lys Ile Lys Pro Thr Ile
        35                  40                  45

Pro Gly Gly Arg Leu Pro Ile Val Lys Ile Thr Asp Lys Arg Gly Asp
    50                  55                  60

Val Lys Thr Met Ser Glu Ser Leu Ala Ile Ala Arg Phe Ile Ala Arg
65                  70                  75                  80

Lys His Asn Met Met Gly Asp Thr Asp Asp Glu Tyr Tyr Ile Ile Glu
                85                  90                  95

Lys Met Ile Gly Gln Val Glu Asp Val Glu Ser Glu Tyr His Lys Thr
            100                 105                 110

Leu Met Lys Pro Pro Glu Glu Lys Glu Lys Ile Ser Lys Glu Ile Leu
        115                 120                 125

```
Asn Gly Lys Val Pro Ile Leu Leu Gln Ala Ile Cys Glu Thr Leu Lys
        130                 135                 140

Glu Ser Thr Gly Asn Leu Thr Val Gly Asp Lys Val Thr Leu Ala Asp
145                 150                 155                 160

Val Val Leu Ile Ala Ser Ile Asp His Ile Thr Asp Leu Asp Lys Glu
                165                 170                 175

Phe Leu Thr Gly Lys Tyr Pro Glu Ile His Lys His Arg Lys His Leu
                180                 185                 190

Leu Ala Thr Ser Pro Lys Leu Ala Lys Tyr Leu Ser Glu Arg His Ala
                195                 200                 205

Thr Ala Phe
        210

<210> SEQ ID NO 6
<211> LENGTH: 218
<212> TYPE: PRT
<213> ORGANISM: Schistosoma japonicum

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys
    210                 215
```